United States Patent
Viola et al.

(10) Patent No.: US 8,664,604 B2
(45) Date of Patent: Mar. 4, 2014

(54) SYSTEM FOR SURVEILLANCE OF AN AREA WITHIN WHICH PEOPLE MOVE

(75) Inventors: Roberto Viola, Rome (IT); Sandro Mengali, Todi (IT); Nicola Liberatore, L'Aquila (IT); Luigi Pierno, Rome (IT)

(73) Assignee: FINMECCANICA—Società per azioni, Rome (IT)

( * ) Notice: Subject to any disclaimer, the term of this patent is extended or adjusted under 35 U.S.C. 154(b) by 0 days.

(21) Appl. No.: 13/581,854

(22) PCT Filed: Mar. 4, 2011

(86) PCT No.: PCT/IB2011/000460
§ 371 (c)(1),
(2), (4) Date: Nov. 8, 2012

(87) PCT Pub. No.: WO2011/107868
PCT Pub. Date: Sep. 9, 2011

(65) Prior Publication Data
US 2013/0206991 A1    Aug. 15, 2013

(30) Foreign Application Priority Data
Mar. 5, 2010   (IT) .............. TO2010A0170

(51) Int. Cl.
*G01J 5/02*   (2006.01)
(52) U.S. Cl.
USPC .................................. 250/339.01

(58) Field of Classification Search
USPC ....................... 250/339.01–339.15
See application file for complete search history.

(56) References Cited

U.S. PATENT DOCUMENTS

2010/0039649 A1* 2/2010 Digonnet et al. ............. 356/460

FOREIGN PATENT DOCUMENTS

| DE | 10 2006 055157 B3 | 4/2008 |
| WO | 01/94915 A1 | 12/2001 |
| WO | 2006/013573 A2 | 2/2006 |
| WO | 2009/157977 A1 | 12/2009 |

* cited by examiner

*Primary Examiner* — Kiho Kim
(74) *Attorney, Agent, or Firm* — Ladas & Parry LLP

(57) ABSTRACT

A system for surveillance of a delimited area within which people move, wherein at least one hollow optical fiber is configured for extending through the area and is provided throughout its length with a plurality of holes that set an internal channel of the fiber in communication with the outside of the fiber itself. There is provided an optical source configured for supplying the optical signal to one end of the hollow optical fiber and a sensor designed to detect at one end of the hollow optical fiber the optical signal transmitted throughout the length of the fiber itself. A processing unit is configured for examining the spectrum of the optical signal detected by the sensors in order to detect the presence of toxic agents present in the area and drawn into said channel.

4 Claims, 2 Drawing Sheets

SYSTEM FOR SURVEILLANCE OF AN AREA WITHIN WHICH PEOPLE MOVE

RELATED APPLICATION INFORMATION

This application is a 371 of International Application PCT/IB2011/000460 filed 4 Mar. 2011 entitled "System For Surveillance Of An Area Within Which People Move", which was published on 9 Sep. 2011, with International Publication Number WO 2011/107868 A1, and which claims priority from Italian Patent Application No. TO2010A000170 filed on 5 Mar. 2010, the content of which is incorporated herein by reference.

TECHNICAL FIELD

The present invention relates to a system for surveillance of:
- an area in which people or goods move;
- the outer perimeter of a predefined area; or
- points sensitive for security of an internal area that are difficult to access, such as, for example, the air-intake and conditioning ducts.

BACKGROUND ART

The need is felt to provide surveillance of crowded areas (for example, airport or sea-port terminals, railway stations, large department stores, shopping centres, industrial plants, etc.) within which people move in order to detect in a timely way the presence of toxic agents in the air present in said area. In these cases, a first-alarm sensor is required that will have the highest likelihood of detection of the substance.

Said toxic agents can be released in the air following upon failures (for example, failures in an industrial plant) or else willful damage such as acts of terrorism.

To meet the need for surveillance referred to above currently used are networks of point sensors (for example, chemical sensors or optical sensors) designed to detect the presence of toxic agents in circumscribed points of the area under surveillance.

Generally these solutions present some limits:
- the use of point sensors entails complexity and high costs since it is necessary to use a large number of interconnected parts;
- the majority of point sensors used does not guarantee a continuous monitoring (for example, they interact with the environment, and require passage from a sampling mode to a cleaning mode);
- point sensors of an optical type can guarantee continuous operativeness, sensitivity and selectivity, but in order to enable all these features to be provided simultaneously they prove too costly to enable their use in a large number.

DISCLOSURE OF INVENTION

The aim of the present invention is to provide a surveillance system of the type referred to above that will be effective, will present high sensitivity and selectivity, will provide a continuous surveillance over time, will have a limited response time, and will present a low cost for its production and installation.

The above aim is achieved by the present invention in so far as it relates to a system for surveillance of a delimited area within which people move, which is characterized in that it comprises:

- at least one hollow optical fibre configured to extend through said area, said hollow optical fibre being provided throughout its length with a plurality of holes that set an internal channel of the fibre in communication with the outside of the fibre;
- conveyor means designed to provide a forced flow of air along said internal channel of the hollow optical fibre;
- optical sources configured for supplying said optical signal to a first end of said hollow optical fibre;
- optical sensors designed to detect the optical signal present at a second end of the fibre;
- optical-coupling means designed to guide an optical signal from the laser source to one end of the hollow optical fibre and from one end of the hollow optical fibre to the sensors;
- connection interfaces designed to convey the optical signal and the flow of air at input to and output from the end of the hollow optical fibre; and
- a system for acquisition, digitalization, and processing of the signal designed to examine the spectrum of the optical signal detected by said sensor means in order to detect the presence of toxic agents present in the area and drawn into said channel, said system comprising a plurality of hollow optical fibres that extend in said area according to a grid structure.

BRIEF DESCRIPTION OF THE DRAWINGS

The invention will now be illustrated with particular reference to the attached drawings, which represent a preferred non-limiting embodiment thereof and in which.

BEST MODE FOR CARRYING OUT THE INVENTION

Figure 1:
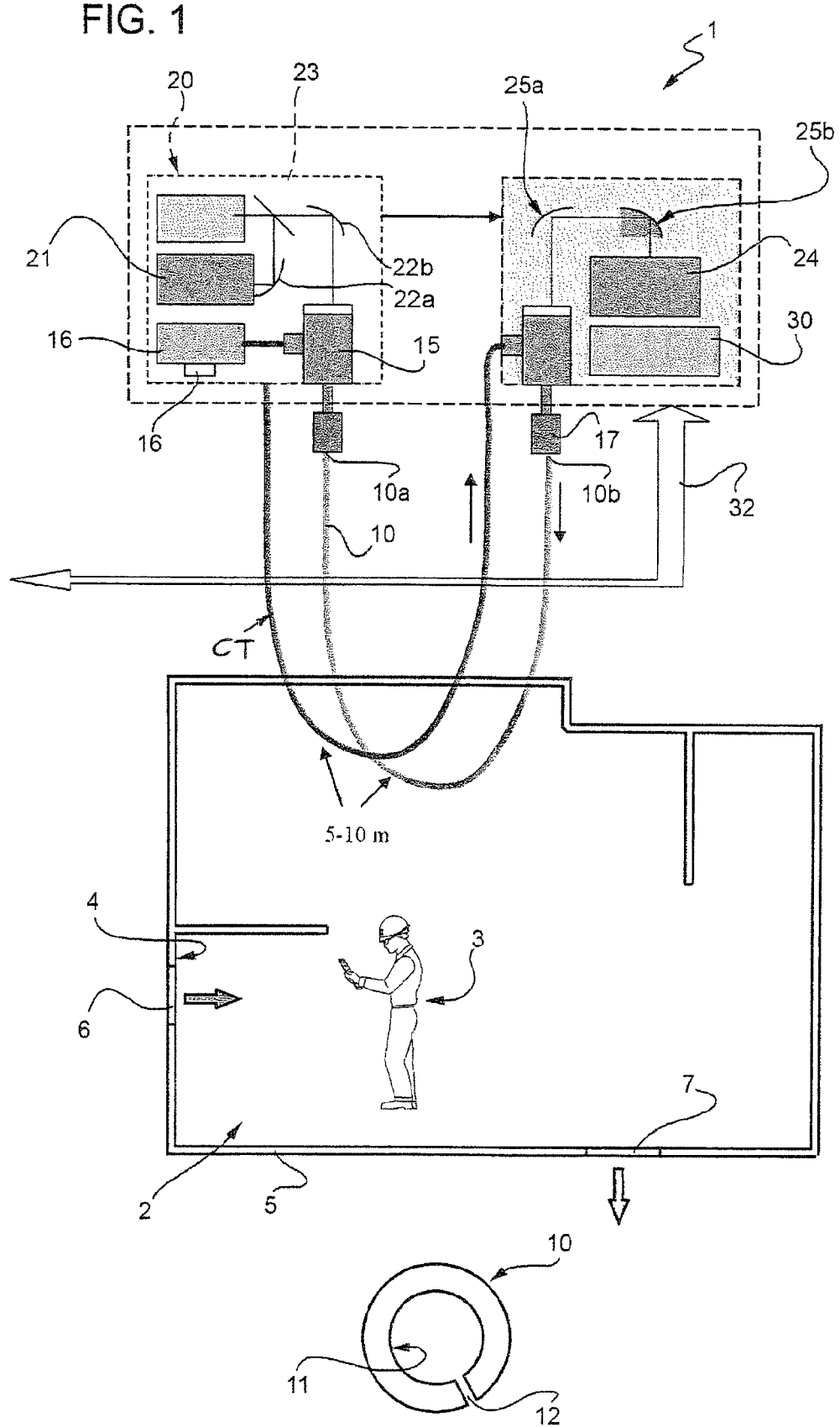
FIG. 1 is a schematic illustration of a system for surveillance of an area within which people move provided according to the dictates of the present invention.

In FIG. 1 designated as a whole by (1) is a system for surveillance of a delimited area (2) within which people move (3).

The area (2) can be conveniently an airport or sea-port terminal, a railway station, a shopping centre, a large department store, or an industrial plant, and comprises at least one compartment (4) delimited by walls (5) (illustrated schematically) and provided with entrances (6) and exits (7).

The system (1) comprises at least one hollow optical fibre (10) (of a commercially available type) configured to extend through the area (2). The hollow optical fibre (10), preferably with a circular cross section, defines an internal channel (11), the hollow optical fibre being provided throughout its length with a plurality of radial holes (12) spaced apart and designed to set the internal channel (11) in communication with the outside of the fibre (10). The radial holes (12) are conveniently provided obtained using technologies of a known type, typically laser drilling.

The hollow optical fibre could also be flanked by a capillary tube CT, which is connected to one end of the fibre and is set alongside it and is provided throughout its length with a plurality of holes that set an internal channel of the tube in communication with the outside of the tube itself.

An example of hollow optical fibre is described in the patent application No. PCT WO 01/94915.

The optical fibre (10) can be rested on the ground, fixed to the walls (5) or else to the ceiling of the area (2), thus adapting to the shape of the compartment (4). Typically the optical fibre (10) can be set in a ventilation duct (not illustrated) of the area (2). The length of the fibre may range from a few meters up to some tens of meters, also by coupling several lengths of hollow optical fibre.

Preferably, the transmittance of the fibre (10) must be such that the signal losses are less than 1 dB/m throughout the operating spectral bandwidth (3 to 15 μm).

The losses due to any bending of the fibre should be less than 1 dB/turn for bends at 90° with radius of curvature greater than 10 cm. If the fibre is laid out, it enables a higher sensitivity of the sensor, as compared to other solutions, thanks to a lower optical loss.

A first end (10a) of the optical fibre (10) is associated to a first connector (15) designed to enable supply of a flow of air within a hollow fibre via a micro-pump (16) of a known type and to enable passage of the optical signal entering the first end of the fibre.

A second end (10b) of the optical fibre (10) is associated to a second connector (17) designed to enable inlet or outlet of the air conveyed in the internal channel (11) by the micro pump (16) and to enable passage of the signal leaving the second end of the fibre.

There is thus obtained a flow of air drawn in from outside the hollow optical fibre along the internal channel (11) from the first end (10a) to the second end (10b) or vice versa. Transmission of the optical signal is moreover enabled from the source (20) to the sensor (24) through the inside of the hollow optical fibre.

The micro-pump (16) is configured for enabling rather fast passage of the air within the fibre 10 with uniform speed, thus minimizing the noise induced by the flow of air within the fibre. The hollow optical fibre (10) and/or the capillary tube CT (if provided) can be provided with a duct that contains them, said duct being able to filter the particulate or to contain the passage of possible interferents towards the inside of the hollow optical fibre and of the capillary tube CT (if present).

The system (1) comprises a generator device (20) for generating an optical signal designed to supply the signal produced to the first end (10a) of the hollow optical fibre (10). For example, the generator device (20) comprises a laser source such as to generate an optical signal with adjustable wavelength, which is guided, by means of two mirrors (22a), (22b) and a beam splitter (23) set between the mirrors, to the first connector (15).

The system (1) further comprises a sensor (24) (of a known type) designed to detect the optical signal present at the second end (10b) of the fibre (10). Said signal is sent to the sensor (24) by means of a pair of mirrors (25a), (25b) that direct towards the sensor (24) the optical signal that exits from the second connector (17). The sensor (24) and the hollow optical fibre (10) preferably operate in the region of the electromagnetic radiation spectrum that ranges from 3 to 15 μm (MID-IR), where the majority of TICs (toxic industrial compounds) and CWAs (chemical war agents) present the most intense characteristic absorption bands (the so-called "fingerprints"). The sensor (24) (which is of a known type) is chosen with short response times.

The system (1) further comprises a processing unit (30), which receives the measurement signal generated by the sensor (24) and a possible reference signal generated by the sensor (21) for processing the optical spectrum of the signal received from the sensor (24).

The processing unit (30) is moreover designed to examine the spectrum of the optical signal (by means of known infrared-spectroscopy algorithms) in order to detect the presence of characteristic shapes of the spectrum that represent toxic agents that are present in the area (2) and are drawn into the channel (11).

In this way, in the case of release of a toxic agent (gas or vapour) within the area (2), said agent is drawn in through the holes (12) of the hollow optical fibre or of the capillary tube CT set alongside it within the channel (11) of the optical fibre (10) where the conditions of light transmission are modified. Consequently, the spectrum of the signal received assumes a characteristic shape that indicates the presence of toxic agents. The electronic unit (30) can then issue an alarm warning on a dedicated line (32) in order to activate the procedures of evacuation of the area (2) and restoring safety conditions.

From the above description the advantages of the system (1) emerge clearly, namely,

- as compared to point sensors, the system (1) enables a substantial reduction of the number of parts and hence of the costs, albeit providing an equivalent or even higher level of coverage;
- as compared to the majority of known systems, the system (1) guarantees a continuous monitoring, and a good sensitivity and selectivity, implementing a wide spectral coverage;
- as compared to point optical sensors, the system (1) is in principle more sensitive, thanks to the optical path provided by the optical fibre and thanks to the higher optical efficiency of transmission of the signal of the hollow optical fibre laid out as compared to point sensors that use the same hollow optical fibre, but wound in a roll, as described in the patent application No. WO2008061949A1; it is estimated that the system (1) can achieve sensitivities in the region of a few ppm without using particularly intense or complex optical sources, and up to a few ppb in the case where laser sources are used; and
- finally, the procedures of alignment and calibration of the system (1) are simpler as compared to those required for a system that uses a number of point sensors.

Figure 2:
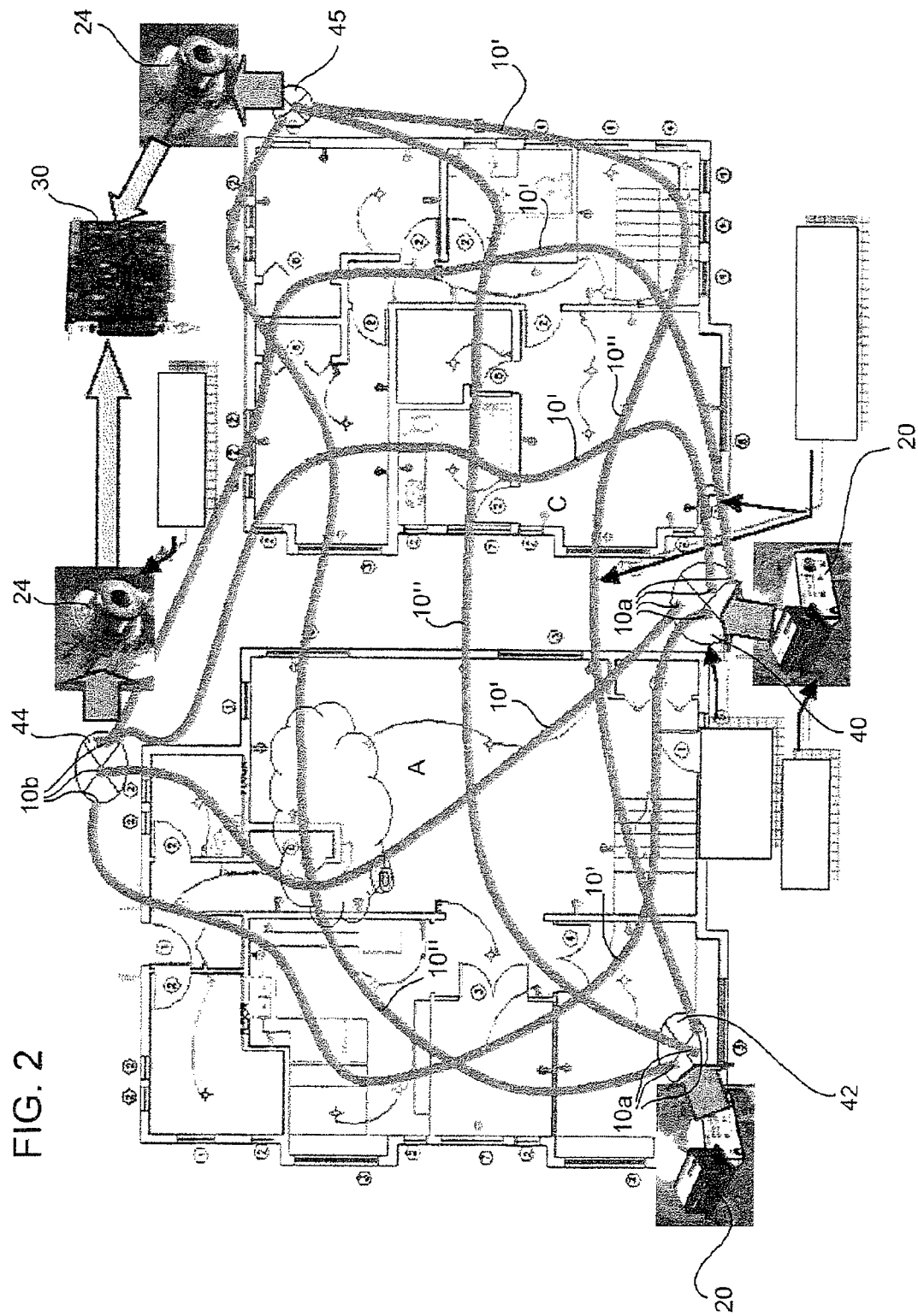
FIG. 2 illustrates a variant to the system of FIG. 1.

FIG. 2 illustrates a plurality of hollow optical fibres that extend in the area (2) according to a grid structure.

In greater detail, the following are provided:
a first de-multiplexer (40) set between the generator device (20) and the first ends (10a) of first fibres (10') for supplying in sequence the optical signal in the first fibres;
a first optical multiplexer (44), which supplies the optical signals present at the second ends (10b) of the first fibres (10') to a first sensor (24); a possible implementation of the optical multiplexer is constituted by a waveguide system of optical switches;
a second de-multiplexer (42) set between a second generator device (20) and the first ends (10a) of second fibres (10") for supplying in sequence the optical signal in the second fibres (10");
the circuit of hollow optical fibres will be equipped with micropumps, one for each fibre, or for each set of fibres supplied by the laser source itself, for adjusting the flow of the air within the hollow optical fibres; a possible but not exclusive implementation consists in a system of pumps and solenoid valves that select the flow from a subset of the optical fibre, for speeding up the analysis of the analyte and/or for increasing the concentration of the gaseous analyte, and restricting the sampling region; and
a second optical multiplexer 45 (of a known type), which supplies the optical signals present at the second ends (10b) of the second fibres (10") to a second sensor (24).

The first and second hollow optical fibres 10', 10" are arranged according to a grid structure in which the first fibres 10' intersect the second fibres 10" in different points A, B, C, etc. of the delimited area 2.

In the case where a toxic substance is released in a point A, B, C, etc. of the area (2) an alarm is detected for at least one first fibre (10') that passes through a given point and for at least one second fibre (10") that passes through the same point. In this way, the electronic unit (30) can recognize the fibres (10',10") involved to the alarm and trace back to the point of intersection of the fibres (10', 10") that is highly likely to correspond to the point of the area (2) in which the chemical attack has been made.

The invention claimed is:

1. A system for surveillance of a delimited area (2) within which people move, characterized in that it comprises:
    at least one hollow optical fibre (10) configured to extend through said area (2), said hollow optical fibre (10) being provided throughout its length with a plurality of holes (12) that set an internal channel (11) of the fibre in communication with the outside of the fibre;
    conveyor means (16) designed to provide a forced flow of air along said internal channel (11) of the hollow optical fibre;
    optical sources (20) configured for supplying said optical signal to a first end (10a) of said hollow optical fibre (10);
    optical sensors (24) designed to detect the optical signal present at a second end (10b) of the fibre;
    optical-coupling means (22a) (22b) (23) (25a) (25b) designed to guide an optical signal from the laser source to one end of the hollow optical fibre and from one end of the hollow optical fibre to the sensors (21) (24);
    connection interfaces (15) (17) designed to convey the optical signal and the flow of air at input to and at output from the end of the hollow optical fibre;
    a system for acquisition, digitalization, and processing of the signal (30) designed to examine the spectrum of the optical signal detected by said sensor means (24) in order to detect the presence of toxic agents present in the area and drawn into said internal channel (11), said system comprising a plurality of hollow optical fibres (10',10") that extend in said area according to a grid structure.

2. The system according to claim 1, wherein multiplexer means or optical switches (40, 42) are provided set between the optical sources (20) and the first ends (10a) of said fibres (10', 10") for supplying in sequence said optical signal in said fibres;
    there being moreover provided optical-adder means (44, 45) that supply the optical signals present at the second ends of the fibres (10', 10") to said sensors (24).

3. The system according to claim 1, wherein there is provided:
    a first plurality of first hollow optical fibres (10') that receive in sequence at their first ends (10a) said optical signal and have second ends (10b) communicating with first sensor means (24); and
    a second plurality of second hollow optical fibres (10"), which receive in sequence at their first ends (10a) said optical signal and have second ends (10b) communicating with second sensor means (24);
    said first and second hollow optical fibres (10', 10") being arranged according to a grid structure in which the first fibres intersect the second fibres in different points of said delimited area;
    a system for acquisition, digitalization, and processing of the signal (30) being provided for detecting the pairs of first optical fibres and second optical fibres for which the presence of a toxic agent has been detected and delimiting the point of said area in which said toxic agent is present.

4. The system according to claim 1, wherein said hollow optical fibre is connected to a capillary tube (CT) flanked by the fibre, provided throughout its length with a plurality of holes that set an internal channel of the capillary tube in communication with the outside of the fibre itself.

* * * * *